(12) United States Patent
Mair et al.

(10) Patent No.: US 10,290,404 B2
(45) Date of Patent: May 14, 2019

(54) METHOD AND APPARATUS FOR NON-CONTACT AXIAL PARTICLE ROTATION AND DECOUPLED PARTICLE PROPULSION

(71) Applicant: WEINBERG MEDICAL PHYSICS LLC, Bethesda, MD (US)

(72) Inventors: Lamar Odell Mair, Washington, DC (US); Aleksandar Nelson Nacev, Bethesda, MD (US); Irving N. Weinberg, Bethesda, MD (US)

(73) Assignee: Weinberg Medical Physics, Inc. MD (US)

( * ) Notice: Subject to any disclaimer, the term of this patent is extended or adjusted under 35 U.S.C. 154(b) by 104 days.

(21) Appl. No.: 14/930,126

(22) Filed: Nov. 2, 2015

(65) Prior Publication Data

US 2016/0125994 A1    May 5, 2016
US 2017/0069416 A9    Mar. 9, 2017

Related U.S. Application Data

(60) Provisional application No. 62/073,360, filed on Oct. 31, 2014, provisional application No. 62/182,901, filed on Jun. 22, 2015.

(51) Int. Cl.
*H01F 1/00* (2006.01)
*A61N 1/40* (2006.01)
(Continued)

(52) U.S. Cl.
CPC .............. *H01F 1/00* (2013.01); *A61N 1/406* (2013.01); *B82B 3/0066* (2013.01);
(Continued)

(58) Field of Classification Search
CPC ........ A61N 1/406; H02N 15/00; H01F 13/00; H01F 7/20; H01F 7/0278
See application file for complete search history.

(56) References Cited

U.S. PATENT DOCUMENTS 4,053,433 A * 10/1977 Lee ....................... C06B 23/008
149/109.4
6,002,314 A    12/1999 Gray
(Continued)

OTHER PUBLICATIONS

Cheang et al.; Minimal geometric requirements for micropropulsion via magnetic rotation; Physical Review; 2014; vol. 90.
(Continued)

*Primary Examiner* — Mohamad A Musleh
(74) *Attorney, Agent, or Firm* — Barnes & Thornburg LLP

(57) ABSTRACT

An apparatus and method for magnetic particle manipulation enables the particle to be rotated and translated independently using magnetic fields and field gradients, which produce the desired decoupled translational and rotational motion. The apparatus and the method for manipulation may be implemented in parallel, involving many particles. The rotational magnetic field used to induce rotational motion may be varied to induce particle motion, which is either in phase or out of phase with the rotational magnetic field. The magnetic fields and gradients described herein may be generated with permanent magnets, electromagnets, or some combination of permanent magnets and electromagnets.

23 Claims, 16 Drawing Sheets

(51) Int. Cl.
*H02N 15/00* (2006.01)
*H01F 7/02* (2006.01)
*H01F 7/20* (2006.01)
*H01F 13/00* (2006.01)
*B82B 3/00* (2006.01)

(52) U.S. Cl.
CPC ............. *H01F 7/0278* (2013.01); *H01F 7/20* (2013.01); *H01F 13/00* (2013.01); *H02N 15/00* (2013.01)

(56) References Cited

U.S. PATENT DOCUMENTS

| | | | | |
|---|---|---|---|---|
| 6,858,184 | B2* | 2/2005 | Pelrine | B01J 19/0046 |
| | | | | 204/193 |
| 7,745,091 | B2* | 6/2010 | True | G01N 33/532 |
| | | | | 430/270.1 |
| 9,532,729 | B2* | 1/2017 | Weissleder | H01F 1/009 |
| 2002/0146745 | A1* | 10/2002 | Natan | G01N 33/538 |
| | | | | 435/7.1 |
| 2004/0209376 | A1* | 10/2004 | Natan | B01J 13/0047 |
| | | | | 436/56 |
| 2007/0172890 | A1 | 7/2007 | Prins et al. | |
| 2007/0197953 | A1 | 8/2007 | Slade et al. | |
| 2008/0044680 | A1* | 2/2008 | Thibodeau | B29C 45/0013 |
| | | | | 428/547 |
| 2009/0306455 | A1 | 12/2009 | Slade et al. | |
| 2010/0259259 | A1 | 10/2010 | Zahn et al. | |
| 2011/0074231 | A1* | 3/2011 | Soderberg | H01F 3/10 |
| | | | | 310/44 |
| 2011/0215888 | A1 | 9/2011 | Abbott et al. | |
| 2011/0301497 | A1 | 12/2011 | Shachar et al. | |
| 2012/0037236 | A1* | 2/2012 | Bertacco | B03C 1/32 |
| | | | | 137/13 |
| 2012/0296149 | A1 | 11/2012 | Creighton | |
| 2013/0206701 | A1 | 8/2013 | Strohmeier et al. | |
| 2014/0309479 | A1 | 10/2014 | Weinberg et al. | |

OTHER PUBLICATIONS

Fan et al.; Controllable High-Speed Rotation of Nanowires; Physical Review Letters; Jun. 2005; vol. 94.
Ghosh et al.; Controlled Propulsion of Artificial Magnetic Nanostructured Propellers; Nano Letters; Jan. 19, 2009.
Ishiyama et al.; Swimming micro-machine driven by magnetic torque; Sensors and Actuators; 2001; vol. 91; pp. 141-144.
Love et al.; Three-Dimensional Self-Assembly of Metallic Rods with Submicron Diameters Using Magnetic Interactions; J. Am. Chem. Soc.; 2003; vol. 125; pp. 12696-12697.
Maali et al.; Nanobubbles and their role in slip and drag; Journal of Physics: Condensed Matter; 2013; vol. 25.
McNaughton et al.; Sudden Breakdown in Linear Response of a Rotationally Driven Magnetic Microparticle and Application to Physical and Chemical Microsensing; J. Phys. Chem; 2006; vol. 110; pp. 18958-18964.
Peyer et al.; Magnetic Helical Micromachines; Chem. Eur. J.; 2013; vol. 19; pp. 28-38.
Silva et al.; Application of hyperthermia induced by superparamagnetic iron oxide nanoparticles in glioma treatment; International Journal of Nanomedicine; 2011; vol. 6; pp. 591-603.
International Preliminary Search Report and Written Opinion for International Patent Application No. PCT/US2015/058617; dated Jan. 19, 2016.
Supplementary European Search Report for International Patent Application No. PCT/US2015/058617; dated Jul. 2, 2018.

\* cited by examiner

METHOD AND APPARATUS FOR NON-CONTACT AXIAL PARTICLE ROTATION AND DECOUPLED PARTICLE PROPULSION

CROSS-REFERENCE TO RELATED APPLICATION APPLICATIONS

This application claims priority under 35 U.S.C. 119(e) to U.S. Provisional Patent Application No. 62/073,360 (incorporated by reference in its entirety) filed on Oct. 31, 2014, entitled "METHOD AND APPARATUS FOR NON-CONTACT AXIAL PARTICLE ROTATION AND DECOUPLED PARTICLE PROPULSION" and to U.S. Provisional Patent Application No. 62/182,901 (incorporated by reference in its entirety) filed on Jun. 22, 2015, entitled "METHOD AND APPARATUS FOR NON-CONTACT AXIAL PARTICLE ROTATION AND DECOUPLED PARTICLE PROPULSION."

FIELD OF THE INVENTION

Disclosed embodiments are directed to a method and apparatus of manipulating magnetic particles.

SUMMARY

Disclosed embodiments provide an apparatus and method for magnetic particle manipulation that enables the particle to be rotated and translated independently using generated magnetic fields and field gradients, which produce the desired decoupled translational and rotational motion.

Disclosed embodiments enable such manipulation of a particle with more than one magnetization direction.

Disclosed embodiments provide an apparatus and method for manipulation that may be implemented in parallel, involving many particles.

Disclosed embodiments provide an apparatus and method for manipulating at least one particle which combines a magnetic gradient for translation of the particle with a magnetic field for rotating at least one particle, the method being used to induce simultaneous particle translation and rotation.

Disclosed embodiments provide and utilize a rotational magnetic field to induce rotational motion, wherein the rotational magnetic field may be varied to induce particle motion, which is either in phase or out of phase with the rotational magnetic field.

Disclosed embodiments provide and utilize magnetic fields and gradients that may be generated with permanent magnets, electromagnets, or some combination of permanent magnets and electromagnets.

BRIEF DESCRIPTION OF THE FIGURES

The detailed description particularly refers to the accompanying figures in which.

DETAILED DESCRIPTION

Figure 1:
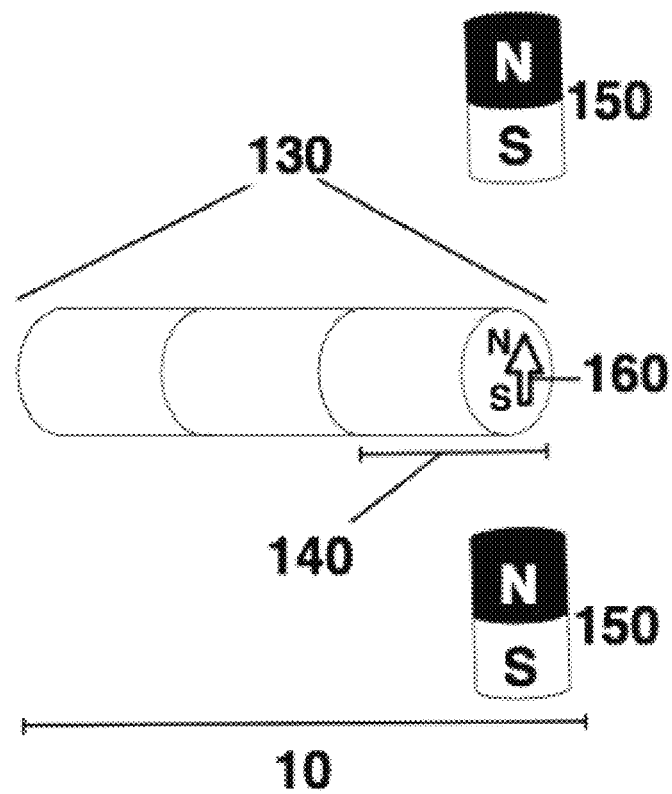
FIGS. 1-4 illustrate an embodiment wherein rotational manipulation is achieved by application of a rotating field with zero or negligible field gradient ($H_{rotating\text{-}zero\text{-}gradient}$).
Figure 2:
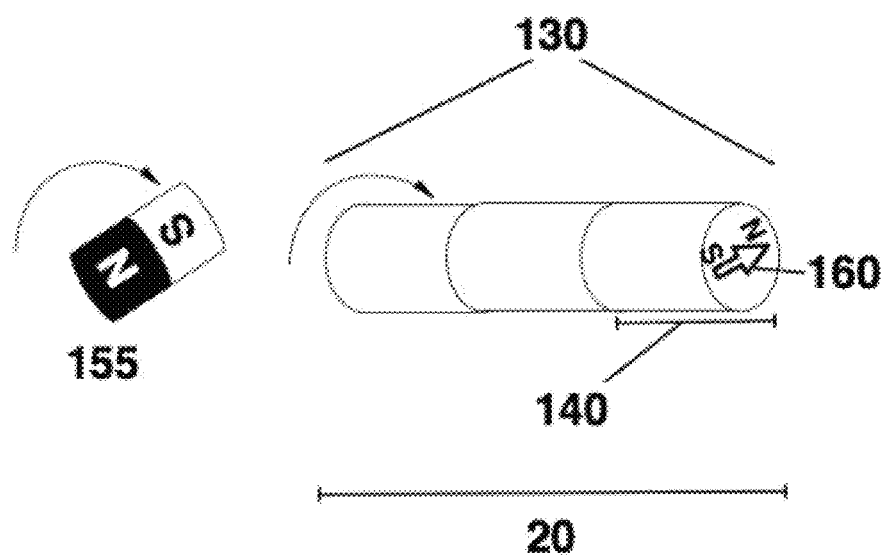
Figure 3:
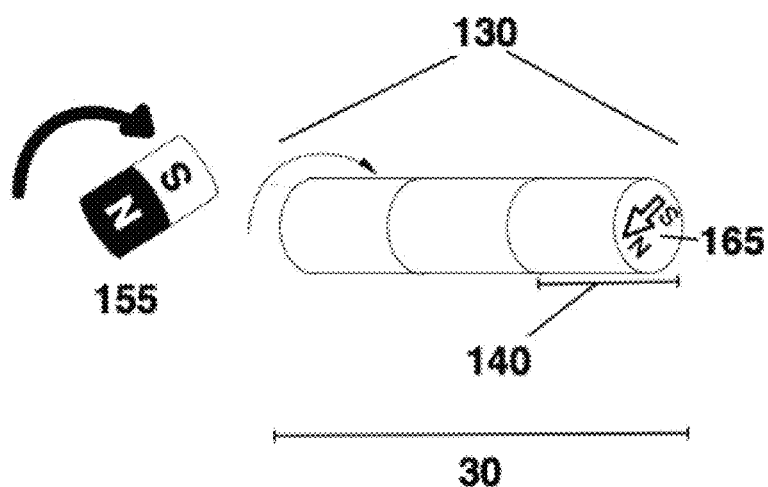

The frequent references to magnetic fields requires a brief index of terms.

A magnetic field with negligible gradient may be referenced as $H_{zero\text{-}gradient}$. If this magnetic field is rotating, it may be referenced as $H_{rotating\text{-}zero\text{-}gradient}$. One example of a rotating field with zero gradient is the field generated by an alternating current carrying coil that is rotated on any axis that is parallel to the face of the coil. By rotating an alternating current carrying wire on an axis parallel to the face of the wire, a zero-gradient magnetic field is generated at the center of the coil.

A magnetic field gradient may be referenced as $H_{with\text{-}gradient}$. If this magnetic field gradient is rotating, then it may be referenced as $H_{rotating\text{-}with\text{-}gradient}$. A rotating magnetic field with a gradient may be generated by rotating an elongated bar magnet around its minor axis (that is, rotating the bar magnet about its lengthwise midpoint).

A magnetic particle has an associated magnetic field, similar to the magnetic field of a common bar magnet. The particle's magnetic field may be referenced as $H_{particle}$.

A magnetic particle also has a magnetization. The particle's magnetization is the magnetic ordering of magnetic domains that compose the particle. The particle's magnetization may be referenced as $M_{particle}$.

A magnetic particle may have two distinct magnetic segments, with each section having its own magnetization direction. In the case of multiple magnetizable segments on the same particle, segment magnetizations may be referred to as $M_{1,particle}$ and $M_{2,particle}$. In the case of a cylindrical particle, $M_{1,particle}$ will refer to magnetization along the long axis of the cylinder and $M_{2,particle}$ will refer to magnetization perpendicular to the long axis of the cylinder.

Disclosed embodiments are directed to a method and apparatus of actuating magnetic particles in which the translational and rotational motions may be decoupled, wherein rotational manipulation is achieved by application of a rotating magnetic field with zero or negligible field gradient ($H_{rotating\text{-}zero\text{-}gradient}$) and translational motion may be achieved by application of a rotating magnetic field gradient ($H_{rotating\text{-}with\text{-}gradient}$) that is aligned parallel or antiparallel to the overall magnetic field of a ferromagnetic particle ($H_{particle}$). A ferromagnetic particle, similar to a common bar magnet, has an associated overall magnetic field ($H_{particle}$). The particle's overall magnetic field ($H_{particle}$) is generated by the magnetic domains contained within the particle. Parallel alignment of any magnetic field gradient ($H_{gradient}$) and the overall particle magnetization ($M_{particle}$) will induce the particle to move in the direction of decreasing gradient, i.e. away from the source of the magnetic gradient ($H_{gradient}$). Antiparallel alignment of the magnetic field gradient ($H_{gradient}$) and the overall particle magnetization ($M_{particle}$) will induce the particle to move in the direction of increasing gradient, i.e. towards the source of the magnetic gradient.

In accordance with disclosed embodiments, a ferromagnetic particle with dimensions between 100 micrometers and 10 nanometers may be made to rotate around one of its axes as a result of a rotating, uniform, applied magnetic field with zero or negligible magnetic gradient ($H_{rotating-zero-gradient}$).

In accordance with disclosed embodiments, rotation of the particle and rotation of the magnetic field ($H_{rotating-zero-gradient}$) may be in phase or out of phase with one another.

In accordance with disclosed embodiments, the composition of the particle may embody many different materials or objects loaded into or onto the particle. These materials or objects may include drugs, proteins, other particles, molecules, or cells. The particle may also include electronic components, including capacitors, resistors, diodes, transistors, or energy-scavenging devices such as glucose fuel cells. Alternatively, disclosed embodiments may use a superparamagnetic particle that may be partially coated with a ferromagnetic component. In the case of a superparamagnetic cylinder coated with a ferromagnetic component, the ferromagnetic component may have magnetic moments perpendicular to the long axis of the particle.

Disclosed embodiments may be implemented in whole or in part to enable rotation of particles for the generation of bubbles and/or vacuum (e.g., cavitation) in close proximity to the particle, utilized in imaging the particle by increasing its effective conspicuity during observation by magnetic resonance, ultrasound, or other known imaging techniques, or used to derive perpendicular magnetizations on a single particle by tuning a length of magnetic sections on a cylindrical particle. The particle may have multiple ferromagnetic or superparamagnetic segments on the same particle. These segments may be magnetically distinct regions, meaning they are separated by a diamagnetic material and that their magnetic domains ($M_{1,particle}$ and $M_{2,particle}$) are independent of one another. Orthogonal magnetization on a single particle refers to a particle having magnetic segments whose magnetic domains (which generate $M_{1,particle}$ and $M_{2,particle}$ generate magnetic fields that exist at an angle of ninety degrees with respect to one another.

Non-contact manipulation of particles can be conventionally achieved by applying magnetic fields to magnetizable particles, as taught by D. L. Fan et al. in the publication titled "Controllable High-Speed Rotation of Nanowires" in the journal Physical Review Letters, Vol. 94, article 247208, June 2005 (incorporated herein by reference in its entirety). Early work on the topic of rotating millimeter scale magnetic materials and devices has focused on chiral materials, as envisioned by K. Ishiyama et al. in their publication "Swimming micro-machine driven by magnetic torque", published in Sensors and Actuators A, Volume 91, pages 141-144, 2001 (incorporated herein by reference in its entirety).

Various papers have demonstrated micro- and nanoscale drills by rotating helical structures, as taught by Ambharish Ghosh and Peer Fischer in the publication "Controlled Propulsion of Artificial Magnetic Nanostructured Propellers", published in the journal Nano Letters, Vol. 9(6), pages 2243-2245, 2009 (incorporated herein by reference in its entirety), and Kathrin E. Peyer et al. in the publication "Magnetic Helical Micromachines" in the journal Chemistry A European Journal, Vol. 19, pages 28-38, 2013 (incorporated herein by reference in its entirety).

In prior art, rotation of the helical particles was accomplished by applying a rotating, uniform magnetic field ($H_{rotating-zero-gradient}$) to the particles. In the cases of the aforementioned microhelical devices (Ghosh and Fischer 2009, Peyer et al. 2013), orientation of the magnetic field ($H_{rotating-zero-gradient}$) is in a direction orthogonal to the particle's intended direction of translation. Additionally, in the cases of microhelical devices, rotation of the device induces translation of the device.

Further, it has been taught by Brandon H. McNaughton et al. in the publication "Sudden Breakdown in Linear Response of a Rotationally Driven Magnetic Microparticle and Application to Physical and Chemical Microsensing" in the Journal of Physical Chemistry B, Volume 110 (38), 2006, pages 18958-18964 (incorporated herein by reference in its entirety), that a magnetic particle in a rotating magnetic field ($H_{rotating-zero-gradient}$) will remain in phase with the magnetic field up to the point at which the magnetic field is not strong enough to drive the rotation of the particle in phase. A rotating magnetic field ($H_{rotating-zero-gradient}$) driving rotating motion in a particle must overcome the force of viscous drag on the particle for the particle to remain in phase with the rotating magnetic field. Because the drag force increases with the rotational velocity of the particle, there exists some frequency at which a given rotating magnetic field becomes insufficient to continue driving rotational motion of the particle in phase with the rotating magnetic field.

When the drag force on the particle becomes larger than the driving force generated by the rotating magnetic field, the particle rotation slips out of phase with the driving magnetic field rotation. This limit is called the "critical slipping point". The point at which critical slipping occurs is due to several factors, primarily the drag imposed on the particle by the surrounding fluid(s) or material(s), the strength of the rotating magnetic field, and the overall magnetic properties of the particle.

With this understanding of the prior art in mind, disclosed embodiments rotate particles in phase with a rotating magnetic field, or out of phase with a rotating magnetic field. Controlled rotation of the particle out of phase with the rotating magnetic field is possible by applying a rotating magnetic field.

Previous applications of magnetically actuated particles as taught by Ghosh et al. and Peyer et al. employed helical coils that relied for propulsion on the coupling of translational and rotational motion. To the contrary, the presently disclosed embodiments provide a method and apparatus of actuating magnetic particles in which the translational and rotational motions may be decoupled.

In this disclosure, it should be understood that geometry described herein and vocabulary used herein are particular to this disclosure. For example, the phrase "major axis" and "minor axis" refer to the axial and radial axes of a cylinder, respectively. The major axis connects the two centers of the bases of the cylinder. The radial axis sits at the midpoint between the two bases of the cylinder, and is parallel to the bases of the cylinder. The cylinder may have any aspect ratio, however for simplicity, the term "major axis" always refers to the axis that connects the centers of the faces of the cylinder. Note that for cylinders that are not right circular cylinders, this major axis may not be perpendicular to the cylinder bases.

FIGS. 1-4 illustrate an embodiment wherein rotational manipulation is achieved by application of a rotating field with zero or negligible field gradient. The rotating field may be supplied by permanent magnets of electromagnetics. Rotational frequencies of 100 Hz to 1000 Hz, or other values, may be applied. In this embodiment, translational motion may be achieved by application of a rotating magnetic field ($H_{rotating-zero-gradient}$) that is aligned parallel to the magnetic field of a ferromagnetic particle ($H_{particle}$). In this orientation the rotation of the particle is induced by the rotating magnetic field. Particle rotation only is achieved when the particle's magnetic field ($H_{particle}$) is in phase with the rotating magnetic field ($H_{rotating-zero-gradient}$). Particle rotation and translation are achieved when the particle's magnetic field ($H_{particle}$) is out of phase with the rotating magnetic field ($H_{rotating-zero-gradient}$) by 180 degrees.

When the rotating magnetic field ($H_{rotating-zero-gradient}$) is adjusted such that it is out of phase with the particle magnetic field ($H_{particle}$) by 180 degrees, the rotating magnetic field's magnetic north is aligned with the particle's magnetic north. The alignment of the rotating magnetic field's "magnetic north" and the particle's "magnetic north" generates a repulsive force that moves the particle away from the source of the rotating magnetic field. The rotating magnetic field's magnetic south direction operates likewise on the particle's magnetic south field. In this configuration, the particle is directed away from the source of the rotating magnetic field, in the direction of decreasing gradient. In this embodiment, the cylinder is diametrically magnetized. Diametric magnetization occurs when the magnetic moment of the cylinder is aligned in a plane parallel to the faces of the cylinder. As a result, the particle is magnetized in the direction of the minor axis of the cylinder.

As shown in FIGS. 1-4, the particle is cylindrical in shape and the particle is diametrically magnetized. However, it should be understood that the same principle could apply to many particle shapes and to particles that are otherwise magnetized.

Moreover, it should be understood that, although a single particle is illustrated in FIGS. 1-4, the disclosed embodiments apply to the manipulation of a plurality of such particles (regardless of shape), for example, an assembly of many such particles.

In accordance with disclosed embodiments, a particle in the nanoscale regime (e.g., 30 nm or less) or larger may be made to rotate around one of its axes as a result of a uniform, rotating magnetic field with zero or negligible magnetic gradient ($H_{rotating-zero-gradient}$).

While [0023] describes an embodiment of the invention in which the driving rotating magnetic field ($H_{rotating-zero-gradient}$) is out of phase with the particle's magnetic field ($H_{particle}$) by 180 degrees, other embodiments may include the particle's magnetic field ($H_{particle}$) being out of phase by some other number of degrees.

As illustrated in FIGS. 1-4, disclosed embodiments utilize at least one particle 130 that embodies at least one magnetic or magnetizable component 140. Particle 130 may be composed of polymers, metals, insulators, semiconductors, ceramics, nanomaterials, or any combinations of these materials. Additionally, particle 130 may be solid, hollow, porous, biphasic, multiphasic, coaxial, or any mixture of these structures. The particle 130 may contain at least one magnetizable section 140 which, for the purposes of illustration, demonstrates magnetization 160 in the direction indicated by the open arrow 160 in FIGS. 1-4. The letters "N" and "S" are used to represent "north" and "south" magnetic poles, respectively, for the applied magnetic fields 150, 155 and the magnetic component of the particle 140.

Thus, FIGS. 1-4 represent a particle 130 in various magnetic fields supplied by magnets 150, 155). Panels 10 (FIG. 1), 20 (FIG. 2), 30 (FIG. 3), and 40 (FIG. 4) represent various points in time. In the present disclosure, it should be understood that the magnetization orientation of the particle 160 may be set through the application of an initial magnetic field, shown in FIG. 1 panel 10, supplied by one or more magnets 150. Prior to being placed in the particle manipulation apparatus, the magnetic or magnetizable segment 140 of the particle may be magnetized, as shown in FIG. 1 panel 10. In the case of the cylindrical particle 130 shown in FIGS. 1-4, the particle magnetization 160 may be in a direction parallel to the face of the cylinder (diametric magnetization).

In a stationary magnetic field, such a particle 130 may align with the magnetic field. In a sufficiently strong and sufficiently slow rotating magnetic field ($H_{rotating-zero-gradient}$), the particle may rotate in phase with the applied magnetic field at 20 (illustrated in FIG. 2). The driving rotating magnetic field and the particle will remain in phase for a given magnetic field, at a given viscosity (surrounding the particle), and a given maximum driving rotating magnetic field ($H_{rotating-zero-gradient}$) frequency. In this configuration at time 20, the particle 130 will remain oriented anti-parallel to, and in phase with, the rotating applied magnetic ($H_{rotating-zero-gradient}$) field 155. As the rotating applied magnetic field 155 ($H_{rotating-zero-gradient}$) is driven by a power source, the rotational frequency of the rotating applied magnetic field ($H_{rotating-zero-gradient}$) may range from less than 100 Hz to more than 1000 Hz.

The rotational frequency of the particle is driven by the rotating magnetic field ($H_{rotating-zero-gradient}$), and is subject to the physical constraints placed on it by the viscosity of the surrounding material, the strength of the magnetic field, and the magnetic properties of the particle. Particle rotation occurring at 20 may be achieved by a rotating magnetic field ($H_{rotating-zero-gradient}$) that has a negligible field gradient. During in-phase rotation at time 20, the magnetic segment 140 of the particle may be aligned anti-parallel 160 to the rotating applied magnetic field 155. As a result, the particle only rotates. As a result, in accordance with disclosed embodiments, translational motion is decoupled from rotational motion. For the purpose of describing the disclosed embodiments, the term "decoupled rotation and translation" of a particle means that rotation and translation can be independently controlled externally to the particle, without substantially changing the shape of the particle.

In accordance with disclosed embodiments, translational motion may be achieved by changing two parameters of the applied rotating magnetic field. In such an implementation, at 30 (illustrated in FIG. 3), the rotational frequency of the rotating magnetic field 155 may be adjusted so that the particle 130 trails the rotating magnetic field 165 by approximately 180 degrees. This can be accomplished by various means, including: increasing the rotating field frequency, decreasing the magnetic field strength, or increasing the viscosity of the material surrounding the particle to increase the drag on the particle as it rotates. Because the rotating magnetic field and the particle's magnetic field are out of phase by approximately 180 degrees, the driving rotating magnetic field and the particle's magnetic field ($H_{particle}$) may be aligned parallel to one another.

Subsequently, at time 40 (FIG. 4), a magnetic gradient 190 may be added to the rotating magnetic field 155. As a result, there may be a repulsive force produced that moves the particle in a direction perpendicular to the vector of the particle's magnetization 165. The repulsive force may be in the direction of decreasing magnetic gradient, as illustrated in FIGS. 1-4. As a result, in accordance with the disclosed embodiments, the rotating magnetic field may drive the particle rotation, and the field gradient may induce translational motion. As a result, in accordance with the disclosed embodiments, rotational motion can be accomplished with or without inducing translational motion.

In accordance with the disclosed embodiments, magnetic fields may be applied by an apparatus of electromagnets and/or permanent magnets described in part or in whole by prior inventions of Dr. Irving Weinberg, including those disclosed in U.S. Pat. Nos. 8,466,680 and 8,154,286 (incorporated by reference herein in their entireties), and related patent applications (by cross-reference, priority or incorporation) filed by the same.

For example, as taught in those disclosures, applied magnetic fields may have very short transition times so as not to cause unpleasant sensations in a body. More specifically, in a prior U.S. patent application Ser. No. 14/873,738 by Aleksandar N. Nacev and Irving N. Weinberg, entitled "Pulsed Gradient Field Method to Counteract a Static Magnetic Field for Magnetic Particle Focusing", filed on Oct. 2, 2015 (incorporated by reference in its entirety), a strategy for propelling particles was disclosed in which magnetizable particles were first polarized and/or aligned in one direction, and then within a short time (e.g., less than the time it would take for polarization to decay) a magnetic field in another direction was applied to the initially polarized particles. As disclosed by Nacev and Weinberg, this strategy could be applied multiple times.

Disclosed embodiments may also be implemented in conjunction with techniques disclosed in US Pat. Pub. 20140309479, entitled "SYSTEM, METHOD AND EQUIPMENT FOR IMPLEMENTING TEMPORARY DIAMAGNETIC PROPULSIVE FOCUSING EFFECT WITH TRANSIENT APPLIED MAGNETIC FIELD PULSES" and filed on Feb. 18, 2014 (incorporated herein by reference in its entirety). Therefore, it should be understood that the disclosed embodiments may be implemented in conjunction with the production and application of magnetic fields to apply repulsive (e.g., diamagnetic) and/or propulsive (e.g., attractive) forces so as to manipulate one or more magnetizable particles, for example by setting up appropriate magnetic gradient fields with or without pre-polarizing pulses.

Additionally, the composition of the particle may embody many different materials or objects loaded into or onto the particle. These materials or objects may include drugs, proteins, other particles, molecules, or cells. The particle may also include electronic components, including capacitors, resistors, diodes, transistors, or energy-scavenging devices such as glucose fuel cells.

Figure 5:
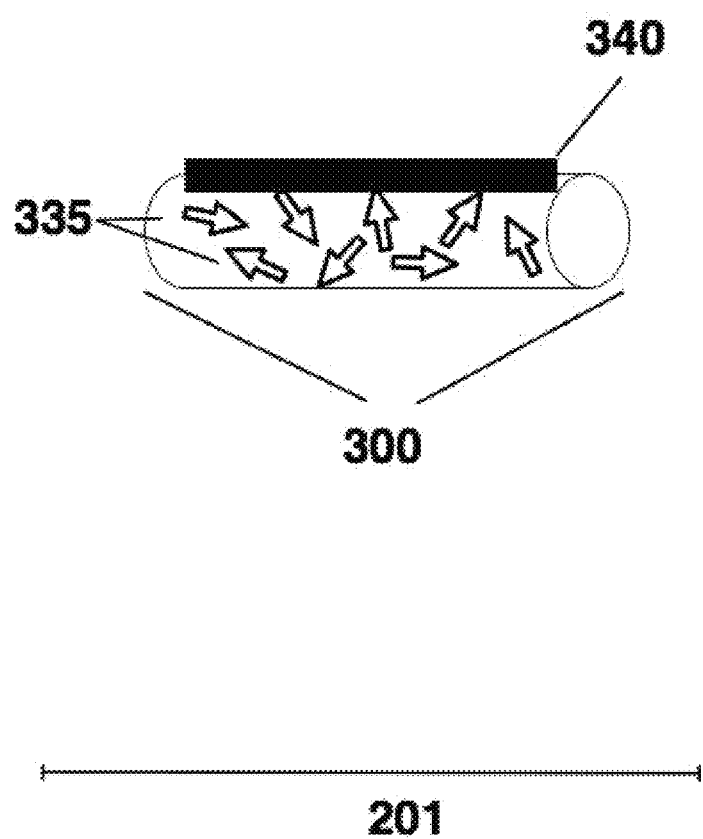
FIGS. 5-6 illustrate an embodiment that may use a superparamagnetic particle that may be partially coated with a ferromagnetic component, the ferromagnetic component being magnetized in a direction perpendicular to the long axis of the particle.
Figure 6:
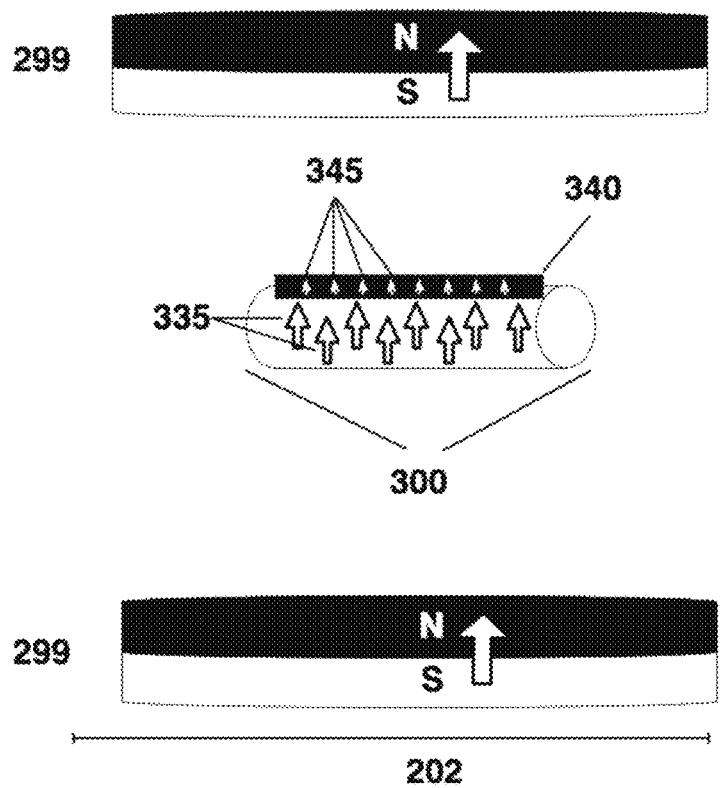
Figure 7:
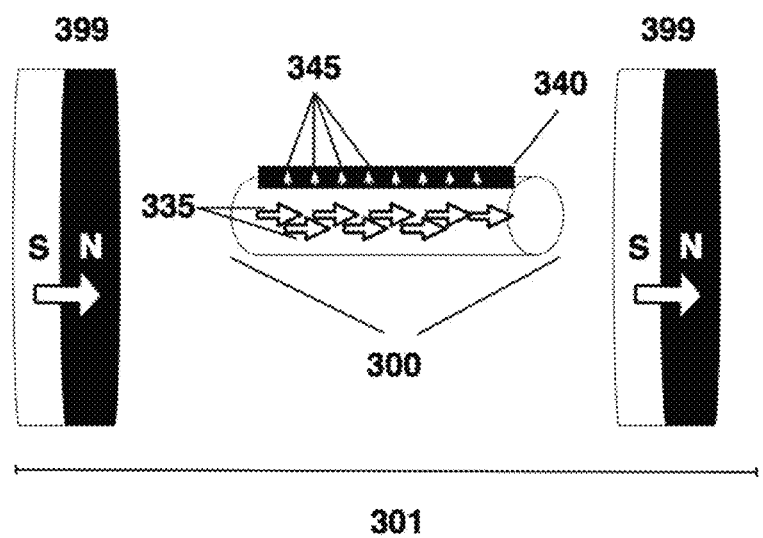
FIGS. 7-8 illustrate how, once a magnetic field is removed, magnetization of the superparamagnetic bulk of the particle illustrated in FIGS. 5-6, undergoes Neelian relaxation (arising due to changes of intrinsic magnetization within the nanoparticles) in accordance with at least one disclosed embodiment.
Figure 8:
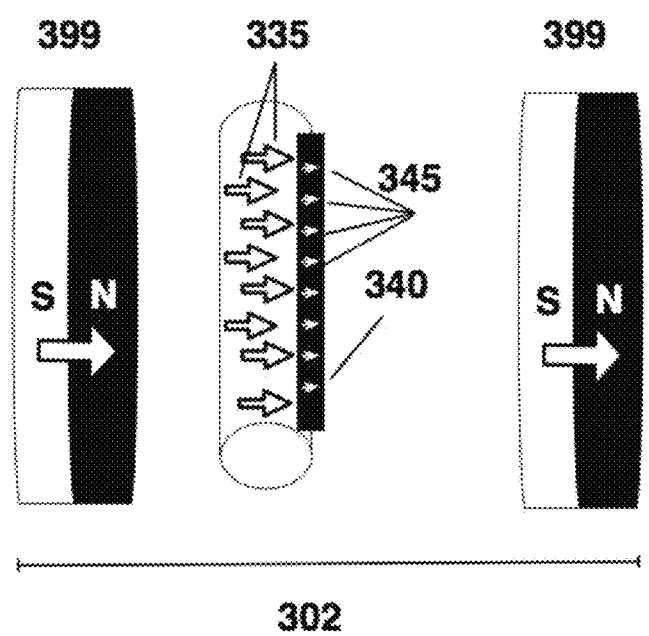

Alternatively, disclosed embodiments may use a superparamagnetic particle that may be partially coated with a ferromagnetic component. The ferromagnetic component may have segments magnetized perpendicular to the long axis of the particle ($M_{2,particle}$). Such a configuration is illustrated in panel 201 illustrated in FIG. 5. In such an embodiment, a ferromagnetic layer 340 may be, volumetrically, only 0.1% of the total volume of the entire particle 300. In one implementation, the bulk of the particle 300 may be composed of a superparamagnetic material having magnetic moments 335 that are randomly oriented outside of a magnetic field. Note that the superparamagnetic portion of the particle 300 will have a segment, very near the ferromagnetic layer 340 that are aligned in parallel with the magnetization of the ferromagnetic layer 340. The magnetic moments of the superparamagnetic material are generally disordered outside of a magnetic field. While the thin ferromagnetic layer 340 does provide some local magnetic field, it is weak and only impacts a small fraction of the magnetic moments of the bulk superparamagnetic material of the particle. Thus, as shown in FIG. 6 the operation of magnetizing the thin ferromagnetic layer magnetic moments 340 may be performed by placing the particle 300 in a magnetic field supplied by magnets 299. As a result, the superparamagnetic bulk magnetic moments 335 of the particle 300 also align with the field. However once the magnet is removed, the magnetization of the superparamagnetic bulk also undergoes Neelian relaxation, as illustrated in FIGS. 7-8.

In at least one embodiment, the particle may take the shape of a cylinder that is longer than it is wide (e.g., aspect ratio greater than 1). In this configuration, there may be interactions among the magnetic moments of the bulk of the particle 300 that may reinforce magnetic alignment of the particle 300 with an applied magnetic field. This force may be in direct opposition to the alignment behavior of the thin ferromagnetic layer 340.

In accordance with at least one disclosed embodiment, the thin ferromagnetic layer magnetic moments 340 may be magnetized diametrically 345 ($M_{2,particle}$); thus, application of at least some designed magnetic fields may induce the long axis of the particle to align perpendicular to the magnetic field.

Moreover, in at least one embodiment of the invention, the long axis of the particle may align antiparallel to the magnetic field for one range of field strengths, and may align perpendicular to the field in another range of field strengths. This may be due to an energy balance of aligning the thin ferromagnetic segment magnetic moments 340 or the bulk superparamagnetic segment magnetic moments 335 of the particle 300 with the magnetic field. Alignment with the superparamagnetic bulk of the particle 300 may prevail when the impetus for dipole-dipole alignment in the superparamagnetic bulk magnetic moments 335 of the particle overcomes the energy barrier of aligning the thin ferromagnetic layer 340 of the particle perpendicular to the magnetic field.

There are two modes of particle alignment. One mode may be referred to as "bulk dominant" alignment mode. Another mode may be referred to as "thin layer dominant" alignment. Bulk dominant alignment and thin layer dominant alignment may result from the application of magnetic fields by magnets 399. Magnets 399 may be electromagnets, permanent magnets, or some combination of both. During bulk dominant alignment, the long axis of the particle may align with the applied magnetic field (illustrated in panel 301 of FIG. 7). During thin layer dominant alignment, the long axis of the particle may align perpendicular to the applied magnetic field (illustrated at panel 302 of FIG. 8).

Figure 4:
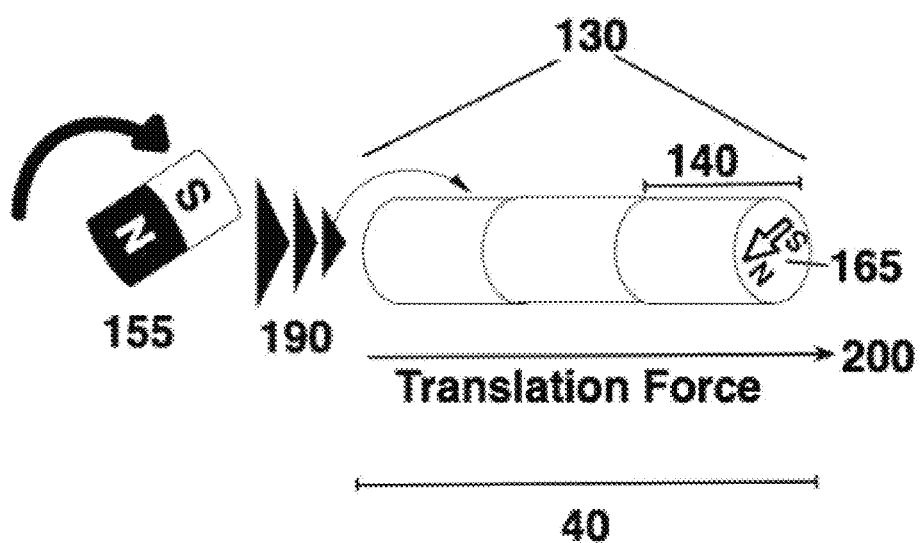
Figure 9:
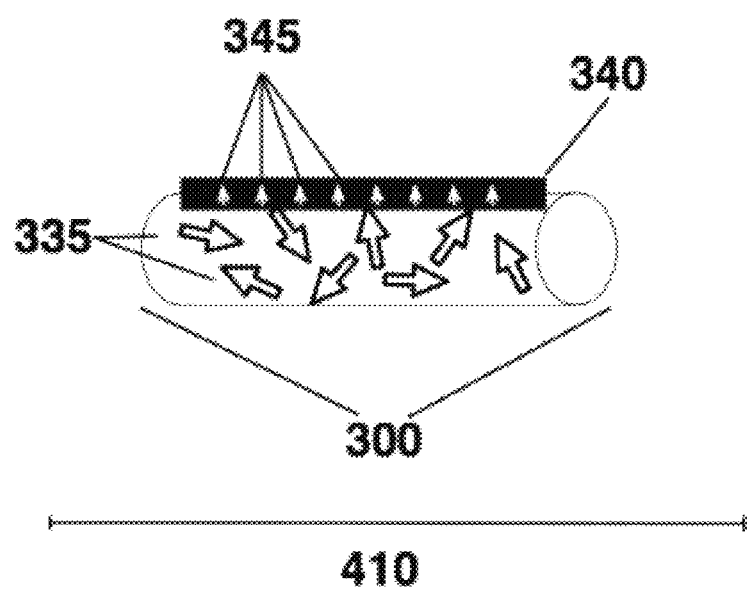
FIGS. 9-14 illustrate a configuration provided in accordance with the disclosed embodiments to provide a combination of rotation and propulsion forces on a particle(s) in accordance with at least one disclosed embodiment.

FIG. 4 illustrates a configuration provided in accordance with the disclosed embodiments to provide a combination of rotation and propulsion forces to a particle or many particles. As shown in panel 410 of FIG. 9, all applied magnetic fields may be removed. As a result, because the bulk of the particle 300 is superparamagnetic, the magnetic moments 335 of the particle bulk may undergo Neel relaxation 335. However, it should be understood that the magnetic moments of the particle ferromagnetic layer undergo negligible Neelian relaxation because they are ferromagnetic.

Figure 10:
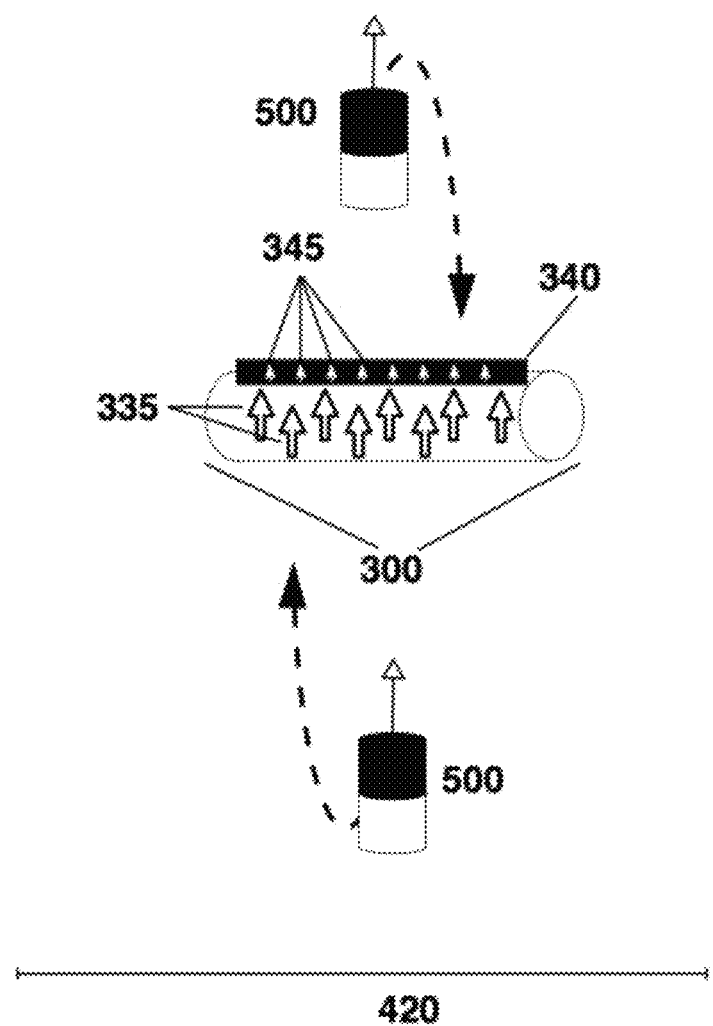

Subsequently, at time or phase 420, a rotational magnetic field 500 may be applied. This rotational magnetic field 500 may make use of the thin layer dominant alignment mode. Thus, at 420 (FIG. 10), a magnetic field is applied that is orthogonal to the long axis of the particle, and parallel to the magnetic moments of the thin ferromagnetic segment 340. Thus, the magnetization of the superparamagnetic segment 335 of the particle 300 may reorder to be arranged perpendicular to the long axis of the particle.

However, significantly, the particle itself does not reorient to align with the magnetic field as in 301 of FIG. 7; this is because the rotational magnetic field 500 is significantly weaker than the aligning magnetic field shown in 301 of FIG. 7. Magnetic fields are additive, thus a rotating magnetic field combined with an aligning magnetic field produces a precessing magnetic field, where precession has some angle away from the axis of the rotating magnetic field.

Figure 11:
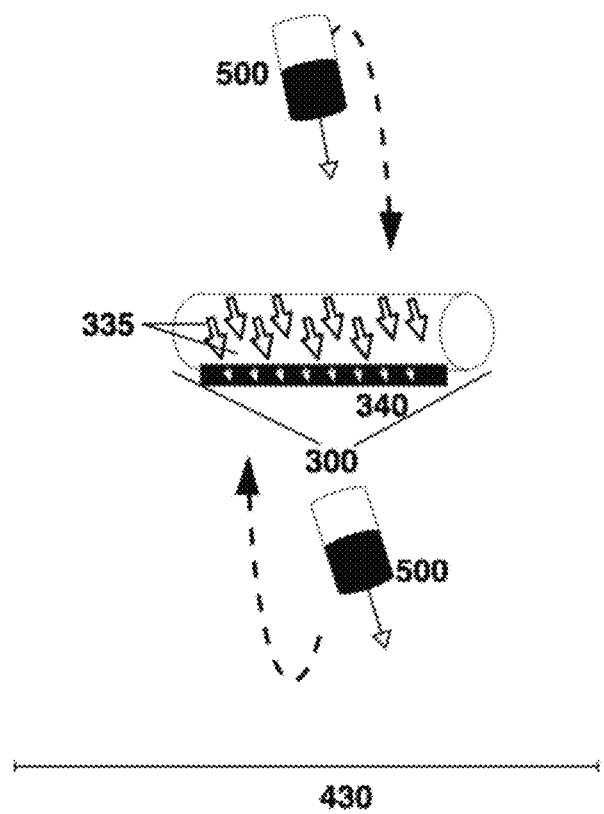

The aligning magnetic field shown in 301 of FIG. 7 may be removed or attenuated and only the rotational magnetic field 500 is present in FIG. 8. Thus, the energetic minimum of the system is achieved by allowing the thin ferromagnetic segment 340 of the particle 300 to be aligned with the rotating magnetic field 500 ($H_{rotating-zero-gradient}$). As shown at 420 (FIG. 10) and 430 (FIG. 11), the particle 300 may be rotated around its long axis because the rotational field 500 is rotated around the long axis of the particle (dotted lines at 420, 430). After application of the rotational field, the rotational field magnets may be removed and the superparamagnetic magnetic moments 335 of the particle bulk may be allowed to undergo Neelian relaxation.

Figure 12:
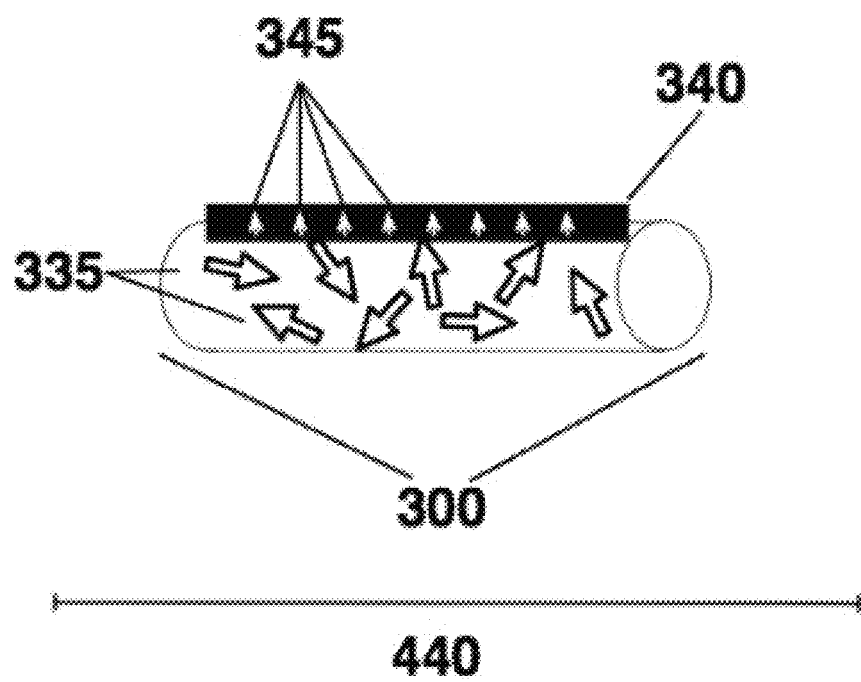
Figure 13:
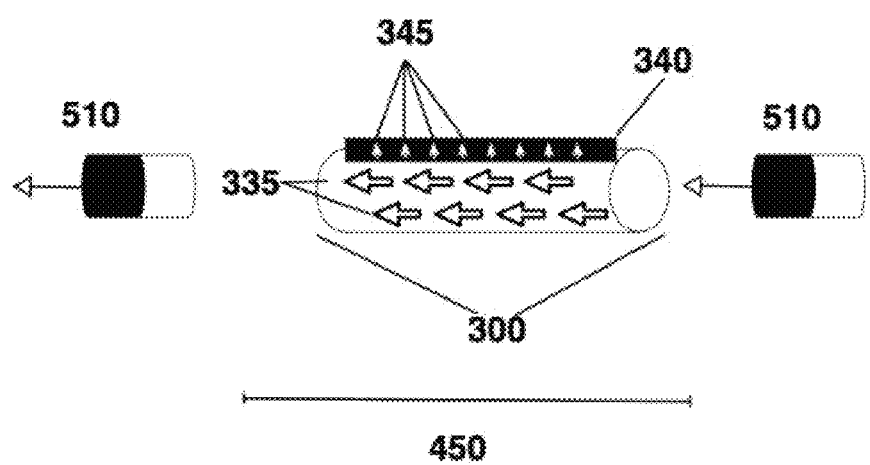
Figure 14:
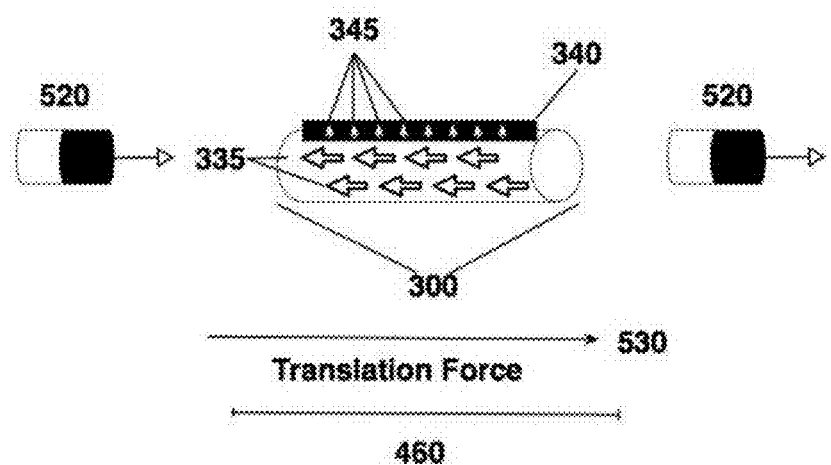

Translational propulsion may be achieved, as shown in panel 440 (FIG. 12), by interleaving the rotating magnetic field 500 ($H_{rotating-zero-gradient}$) applied in panels 420 (FIG. 10) and 430 (FIG. 10), with the propulsion magnetic field ($H_{zero-gradient}$) application shown in panels 450 (FIG. 13) and 460 (FIG. 14). By applying a strong magnetic field gradient ($H_{zero-gradient}$) using magnets 510, the superparamagnetic bulk of the particle will have magnetic moments 335 that temporarily align antiparallel to the strong alignment magnetic field produced by a pair of magnets 510. It should be understood that the alignment field produced by the magnets 510 in FIG. 13 could be implemented through the application of electromagnets or permanent magnets.

Overall physical alignment of the particle 300 in space may be achieved by a strong aligning magnetic field. During the application of the strong aligning magnetic field the superparamagnetic moments 335 of the particle volume may energetically favor aligning with the field along the long axis of the particle 300. Due to the particle 300 being primarily composed of superparamagnetic material, the energetic minimum may be obtained by the particle 300 aligning with the strong aligning magnetic field produced by magnets 510. To the contrary, the ferromagnetic component 340 may have magnetic moments 345 orthogonal to the strong aligning magnetic field. This is due to the overwhelming aligning force caused by the superparamagnetic moments 335 of the particle bulk energetically favoring alignment at 450 with the magnetic field.

Propulsion may be achieved by removal of the aligning magnetic field magnets 510 ($H_{zero-gradient}$) and applying a fast pulse of magnetic field gradient ($H_{with-gradient}$) in the direction antiparallel 520 to the aligning magnetic field. The result may be a propulsion force 530, similar to that previously disclosed by Aleksandar Nacev and Irving Weinberg.

In such an embodiment, with reference to FIGS. 9-14, operations performed in panels 410-460 may represent sequential points in time. These operations may interleave the strong aligning magnetic field and the rotational magnetic field to achieve alignment and rotational manipulation of the particle at 430. Thus, in at least this embodiment, rotation and translation may be accomplished by interweaving magnetic pulses for sequentially aligning the particle, translating the particle via a parallel or antiparallel aligned magnetic field gradient ($H_{with-gradient}$), and rotating the particle with a rotating magnetic field having zero or negligible gradient ($H_{rotating-zero-gradient}$).

Applications of the disclosed embodiments are varied. Tissues and fluids in the body are non-Newtonian materials with viscoelastic properties that hinder motion of particles under magnetic guidance. It is known that very small bubbles can alter the motion of particles in viscous fluids, as taught by A. Maali and B. Bhushan in the article entitled "Nanobubbles and their role in slip and drag", published in the Journal of Physics: Condensed Matter 25 (2013) pp. 184003 (incorporated by reference in its entirety).

The presently disclosed embodiments may be implemented in whole or in part to enable rotation of particles for the generation of bubbles and/or vacuum (e.g., cavitation) in close proximity to the particle. Cavitation may, thus, be used to lubricate the particle, serving as a low resistance boundary between the particle surface and surrounding media. In an additional embodiment, cavitation may aid in imaging the particle by increasing its effective conspicuity during observation by magnetic resonance, ultrasound, or other known imaging techniques discussed in references cited and incorporated herein.

In an additional embodiment, rotation may be utilized in imaging the particle by increasing its effective conspicuity during observation by magnetic resonance, ultrasound, or other known imaging techniques discussed in references cited and incorporated herein. For example, rotation of the particle may affect its absorption or reflectance of energy impinging on the particle from a source.

Figure 15:
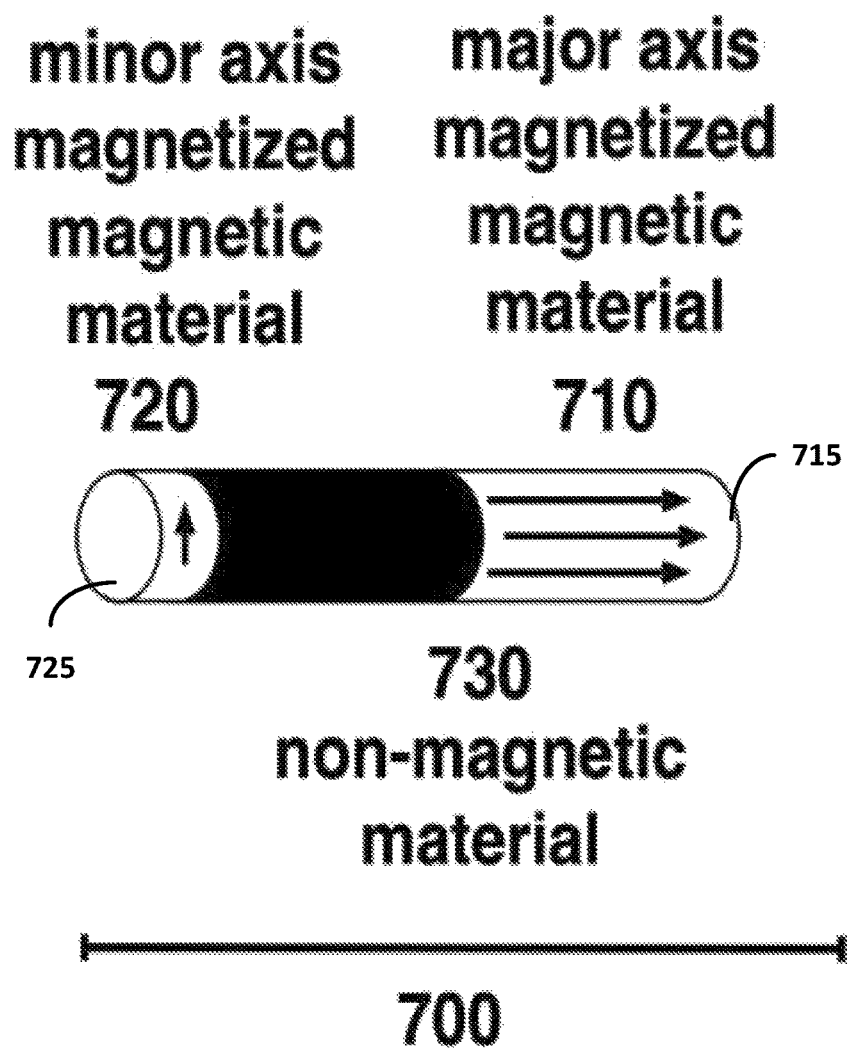
FIG. 15 illustrates a cylinder with a magnetic segment with a length more than twice the cylinder diameter having a magnetization axis along the length of the cylinder in accordance with at least one disclosed embodiment.

Additionally, disclosed embodiments may be utilized to increase the coupling efficiency of sections of a particle to applied magnetic fields by manufacturing one or more magnetic sections of a particle with specified lengths or ratios of lengths. As an example, as illustrated in FIG. 15, a cylinder with a magnetic segment with a length more than twice the cylinder diameter will have an easy axis of magnetization along the length of the cylinder. The relationship of rod length to the ease of magnetization in a particular direction is taught by Love et al. in their publication "Three-Dimensional Self-Assembly of Metallic Rods with Submicron Diameters Using Magnetic Interactions" published in the Journal of the American Chemical Society 125, 12696-12697, 2003 (incorporated herein by reference in its entirety).

One method of accomplishing magnetic segments on cylinders magnetized perpendicular to the long axis (M2, particle) of the cylinder may be by making the magnetic segment shorter than the diameter of the cylinder itself. Thus, cylinders with perpendicular magnetizations M1, particle and M2, particle may be manufactured by creating at least two magnetic segments on a single cylinder, as illustrated in phase 700 of FIG. 15. Thus, one or many magnetic segments with lengths of at least twice the cylinder diameter 710 (M1, particle), and one or many segments with lengths less than the cylinder diameter 720 (M2, particle) may be provided, each magnetic segment being separated by nonmagnetic material 730. As illustrated in FIG. 15, arrows indicate the direction of magnetization of each segment 715, 725.

Figure 16:
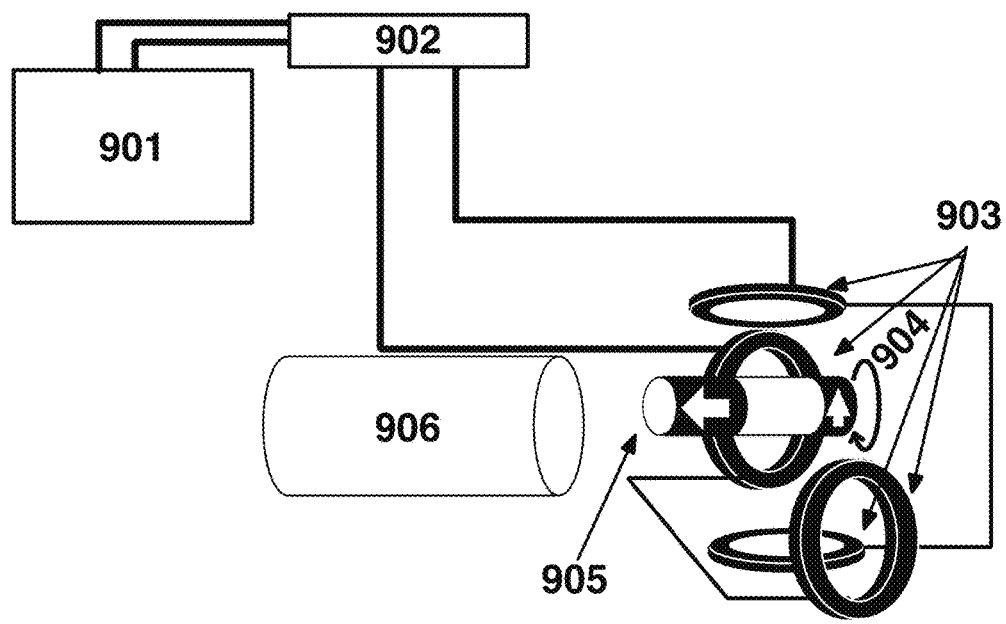
FIG. 16 illustrates one example of operation of an apparatus provided in accordance with the disclosed embodiments.

FIG. 16 illustrates one example of operation of an apparatus provided in accordance with the disclosed embodiments. As shown in FIG. 16, a plurality (e.g., four) of electromagnets 903 are provided with one permanent magnet 906 to manipulate the particle 905 in the prescribed manner. Note that the electromagnets in FIG. 16 may supply the magnetic field with zero or negligible gradient. Also, note that the particle shown in FIG. 16 may have two magnetizations embodied on the single particle. Each magnetization direction is shown with an arrow on the body of the particle 905. In operation, the apparatus incorporates and utilizes a computer 901 to generate a signal for driving the four electromagnets 903. The computer 901 may be replaced by another signal generating device capable of supplying current to electromagnets 903. For example, a pulsed voltage supply may be used. The signal generated by the computer 901 may be amplified by an amplifier 902, before being sent to the electromagnets 903.

FIG. 16 further illustrates that the electromagnets may be driven by a two-channel signal; however, the demonstration of two channels is only intended to be exemplary. It should be understood that the disclosed embodiments may include two electromagnets, eight electromagnets, or more. Likewise, the electromagnets may be driven by one channel of signal from computer 901 or other signal generator, eight channels of signal from the computer 901 or other signal generator, or more channels. Additionally, electromagnets may be used to excite particles using RF pulses for heating the particles to locally induce hyperthermia.

FIG. 16 demonstrates rotation around the long axis of the rod 904 produced by the rotating field supplied by the electromagnets 903. A permanent magnet 906 may be used to provide a magnetic gradient. It should be understood that this magnetic gradient may be generated using an electromagnet, and may vary in amplitude and frequency over the course of time.

It should be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of components (e.g., magnets) of an instrument for applying magnetic fields described herein to manipulate one or more particles may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Accordingly, such an instrument may include one or more controllable electromagnetic field sources and a controller that enables control of resulting magnetic fields as described herein. In one such implementation, one or more gradient coils may be utilized under the control of a controller to enables control of the gradient to produce one or magnetic fields using at least one coil driver, wherein one or more coils are provided for transmitting RF energy into a tissue sample of a body part as part of diagnostic, prognostic, and/or treatment Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments of the present invention. Such alternative storage devices should be considered equivalents.

In accordance with at least one embodiment, apparatuses and methods are provided for rotating and translating a particle, in which at least some portion or component of the particle contains a magnetizable material, and in which the rotation of the particle is decoupled from the translational motion of the particle. For the purposes of this disclosure, the term "decoupled" is intended to mean the ability to vary the ratio between the translational velocity and the rotational velocity of the particle. This decoupling is different from the prior art, for example in which magnetic particles have been manufactured or configured in screw or arc shape so as to drill into or through a medium. In that example, the ratio of translational velocity to the rotational velocity is not variable, since it is set by the geometric configuration of the screw or arc. An example of the prior art was presented by UK Cheang, F Meshkali, D Kim, M J Kim, and H C Fu, at the 2014 article of the journal Physical Review E (volume 90, 033007), entitled "Minimal geometric requirements for micrpropulsion via magnetic rotation".

In accordance with at least one embodiment, the particle may have segments with features having dimensions on the order of 1 nanometer or more in any dimension.

In accordance with at least one embodiment, the rotational field applied to the particle may range from 1 Hz to 1000 Hz.

In accordance with at least one embodiment, electromagnets used to manipulated particles may be operated so as to generate alternating magnetic fields. The electromagnets may be operated at radio frequencies, and the operation may be used to excite rapid changes in the magnetic domains of the particles. The rapid changes in the particle's magnetic domains may be used to convert the rapidly switching magnetic energy into thermal energy, emitted from the particle.

In accordance with at least one embodiment, the particle may be composed of polymeric, metallic, insulating, semiconducting, ceramic, or any combinations of these materials. In accordance with at least one embodiment, the particle may house electronics, molecules/drugs, proteins, cells, or energy scavenging components.

In accordance with at least one embodiment, the particles may carry segments capable of emitting light (for example by carrying phosphorescent material), or are capable of being heated using RF fields for supplying thermal energy for hyperthermia treatments. Magnetic particle induced hyperthermia is the process by which alternating magnetic fields are used to excite magnetic particles placed in a human or animal body. Alternating field excitation may be performed at radio frequencies. Particle excitation induces particle heating. This heating may be used to damage or kill cells in the vicinity of the particles. By localizing the magnetic particles using magnetic fields and field gradients, the released thermal energy can be targeted to the region around the particles, as taught by Andre C. Silva et al., in the publication "Application of hyperthermia induced by superparamagnetic iron oxide particles in glioma treatment," published in the International Journal of Nanomedicine, Volume 6, pages 591-603, 2011.

In accordance with at least one embodiment, rotation of the particle reduces effective resistance to motion. A reduction in the effective resistance to motion may be achieved by locally reducing the effective viscosity of the surrounding biological materials, tissues, or fluids. For example, tissue is a shear thinning material. This means that the effective viscosity of tissue decreases as the shear applied to the tissue increases. Rotation of the particle generates a shear force around the particle, and this shear force may decrease the effective viscosity of the tissue surrounding the particle. Additionally, the applied shear force may result in barriers to motion, such as dense agglomerations of proteins or plaques, to be moved due to the induced shear force. Alternatively, the shear force may be used to induce translation of the particle in a direction perpendicular to the direction of translation.

In accordance with at least one embodiment, rotation of the particle increases conspicuity under imaging. In accordance with at least one embodiment, a solution contains multiple particles and/or multiple different types of particles, i.e., collections of particles housing electronics, and/or collections of particles containing molecules/drugs, and/or collection of particles operating as energy scavenging components. In accordance with at least one embodiment, rotation of the particle increases translational velocity in a medium. The medium may be Newtonian or non-Newtonian. In accordance with at least one embodiment, if the particle is carrying a payload (e.g., a drug), then rotation of the particle modifies the rate of release of the payload. In accordance with at least one embodiment, rotation of the particle modifies the rate or mode of degradation of the particle, for example by stressing the junctions between portions of the particle.

Illustrated embodiments include an apparatus for rotating and translating at least one particle, the apparatus comprising: means for generating magnetic force and torque; and at least one particle, wherein at least some portion of the at least one particle contains a magnetizable material, wherein the generated magnetic force is applied to at least some portion of the at least one particle to cause translational motion of the particle, wherein the generated magnetic torque is applied to at least some other portion of the same at least one particle to cause rotation of the particle, and wherein the ratio of the translational and rotational velocities of the particle is varied.

Illustrated embodiments include such an embodiment, wherein the particle is introduced in a body, and a ratio of the translational and rotational velocities of the particle is varied while the particle is in the body.

Illustrated embodiments include such an embodiment, wherein the means for generating magnetic force includes means for generating a rotational field ranging from 1 Hz to 1000 Hz.

Illustrated embodiments include such an embodiment, wherein the at least one particle is composed of polymeric, metallic, insulating, semiconducting, ceramic, or combinations of at least two of these materials.

Illustrated embodiments include such an embodiment, wherein the at least one particle houses electronics, molecules/drugs, proteins, cells, or energy scavenging components.

Illustrated embodiments include such an embodiment, wherein the at least one particle carries segments capable of emitting light.

Illustrated embodiments include such an embodiment, wherein the at least one particle is capable of being heated using radiofrequency radiation.

Illustrated embodiments include such an embodiment, wherein the at least one particle is capable of being heated using alternating magnetic fields.

Illustrated embodiments include such an embodiment, wherein the at least one particle is capable of carrying a payload.

Illustrated embodiments include such an embodiment, wherein rotation of the at least one particle reduces effective resistance to motion.

Illustrated embodiments include such an embodiment, wherein rotation of the at least one particle increases conspicuity under imaging.

Illustrated embodiments include such an embodiment, wherein rotation of the at least one particle increases translational velocity in a medium.

Illustrated embodiments include such an embodiment, wherein rotation of the at least one particle modifies release of a payload contained in the at least one particle.

Illustrated embodiments include such an embodiment, wherein rotation of the at least one particle modifies degradation of the at least one particle.

Illustrated embodiments include such an embodiment, wherein at least one of the rotation of the at least one particle and the decoupled translational motion of the at least one particle are implemented in conjunction with the production and application of magnetic fields to apply repulsive and/or propulsive forces so as to manipulate the at least one particle. Illustrated embodiments include such an embodiment, wherein manipulation of the at least one particle is performed by setting up appropriate magnetic gradient fields with or without pre-polarizing pulses.

Illustrated embodiments include such an embodiment, further comprising a solution that contains a plurality of particles including the at least one particle, wherein each particle of the plurality of particles includes some portion or component that contains a magnetizable material, wherein magnetic torque causing rotation of each of the plurality of particle is decoupled from the magnetic force causing translational motion.

Illustrated embodiments include such an embodiment, where an amplitude and frequency of a magnetic field causing rotation of the at least one particle is independent of an amplitude and frequency of a magnetic gradient that is causing translation of the at least one particle. Illustrated embodiments include such an embodiment, wherein the amplitude of the magnetic gradient used to induce the at least one particle translation is constant in time. Similarly, illustrated embodiments include such an embodiment, wherein the amplitude of the magnetic gradient changes in time.

Illustrated embodiments include a method for rotating and translating at least one particle, the method comprising: generating and applying a magnetic force and torque upon at least one particle, wherein the at least one particle includes at least two segments, each of which contains a magnetizable material; applying the magnetic force to at least one segment in order to cause translational motion of the particle; and applying the magnetic torque to at least one other segment in order to cause rotational motion of the particle, wherein a ratio of the resultant translational and rotational velocities of the particle is varied.

Illustrated embodiments include such an embodiment, wherein the particle is introduced in a body, and a ratio of the translational and rotational velocities of the particle is varied while the particle is in the body.

Illustrated embodiments include such an embodiment, wherein the generation of the magnetic force generates a rotational field ranging from 1 Hz to 1000 Hz.

Illustrated embodiments include such an embodiment, wherein the at least one particle is composed of polymeric, metallic, insulating, semiconducting, ceramic, or combinations of at least two of these materials.

Illustrated embodiments include such an embodiment, wherein the at least one particle houses electronics, molecules/drugs, proteins, cells, or energy scavenging components.

Illustrated embodiments include such an embodiment, wherein the at least one particle carries segments capable of emitting light.

Illustrated embodiments include such an embodiment, wherein the at least one particle is capable of being heated using radiofrequency radiation.

Illustrated embodiments include such an embodiment, wherein the at least one particle is capable of being heated using alternating magnetic fields.

Illustrated embodiments include such an embodiment, wherein the at least one particle is capable of carrying a payload.

Illustrated embodiments include such an embodiment, wherein rotation of the at least one particle reduces effective resistance to motion.

Illustrated embodiments include such an embodiment, wherein rotation of the at least one particle increases conspicuity under imaging.

Illustrated embodiments include such an embodiment, wherein rotation of the at least one particle increases translational velocity in a medium.

Illustrated embodiments include such an embodiment, wherein rotation of the at least one particle modifies release of a payload contained in the at least one particle.

Illustrated embodiments include such an embodiment, wherein rotation of the at least one particle modifies degradation of the at least one particle.

Illustrated embodiments include such an embodiment, wherein at least one of the rotation of the at least one particle and the decoupled translational motion of the at least one particle are implemented in conjunction with the production and application of magnetic fields to apply repulsive and/or propulsive forces so as to manipulate the at least one particle.

Illustrated embodiments include such an embodiment, wherein manipulation of the at least one particle is performed by setting up appropriate magnetic gradient fields with or without pre-polarizing pulses.

Illustrated embodiments include such an embodiment, wherein the at least one particle is one of a plurality of particles, wherein each particle of the plurality of particles includes some portion or component that contains a magnetizable material, wherein magnetic torque causing rotation of each of the plurality of particle is decoupled from the magnetic force causing translational motion.

Illustrated embodiments include such an embodiment, wherein a solution that contains a plurality of particles including the at least one particle, wherein each particle of the plurality of particles includes some portion or component that contains a magnetizable material, wherein magnetic torque causing rotation of each of the plurality of particle is decoupled from the magnetic force causing translational motion.

Illustrated embodiments include such an embodiment, wherein an amplitude and frequency of a magnetic field causing rotation of the at least one particle is independent of an amplitude and frequency of a magnetic gradient that is causing translation of the at least one particle. Illustrated embodiments include such an embodiment, wherein the amplitude of the magnetic gradient used to induce the at least one particle translation is constant in time. Similarly, illustrated embodiments includes such an embodiment, wherein the amplitude of the magnetic gradient changes in time.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

We claim:

1. An apparatus for rotating and translating at least one particle, the apparatus comprising:
    means for generating magnetic force and torque; and at least one particle,
    wherein at least some portion of the at least one particle contains a magnetizable material,
    wherein the generated magnetic force is applied to at least some portion of the at least one particle to cause translational motion of the particle,
    wherein the generated magnetic torque is applied to at least some other portion of the same at least one particle to cause rotation of the particle,
    wherein magnetic torque causing rotation of the at least one particle is decoupled from the magnetic force causing translational motion of the at least one particle, and
    wherein the ratio of the translational and rotational velocities of the particle is variable.

2. The apparatus of claim 1, wherein the particle is introduced in a body, and a ratio of the translational and rotational velocities of the particle is varied while the particle is in the body.

3. The apparatus of claim 1, wherein the means for generating magnetic force includes means for generating a rotational field ranging from 1 Hz to 1000 Hz.

4. The apparatus of claim 1, wherein the at least one particle is composed of polymeric, metallic, insulating, semiconducting, ceramic, or combinations of at least two of these materials.

5. The apparatus of claim 1, wherein the at least one particle houses electronics, molecules/drugs, proteins, cells, or energy scavenging components.

6. The apparatus of claim 1, wherein at least one of the rotation of the at least one particle and the decoupled translational motion of the at least one particle are implemented in conjunction with the production and application of magnetic fields to apply repulsive and/or propulsive forces so as to manipulate the at least one particle.

7. The apparatus of claim 1, wherein manipulation of the at least one particle is performed by setting up appropriate magnetic gradient fields with or without pre-polarizing pulses.

8. The apparatus of claim 1, wherein the at least one particle is one of a plurality of particles, wherein each particle of the plurality of particles includes some portion or component that contains a magnetizable material, wherein magnetic torque causing rotation of each of the plurality of particle is decoupled from the magnetic force causing translational motion.

9. The apparatus of claim 1, further comprising a solution that contains a plurality of particles including the at least one particle, wherein each particle of the plurality of particles includes some portion or component that contains a magnetizable material, wherein magnetic torque causing rotation of each of the plurality of particle is decoupled from the magnetic force causing translational motion.

10. The apparatus of claim 1, where an amplitude and frequency of a magnetic field causing rotation of the at least one particle is independent of an amplitude and frequency of a magnetic gradient that is causing translation of the at least one particle.

11. A method for rotating and translating at least one particle, the method comprising:
generating and applying a magnetic force and torque upon at least one particle, wherein the at least one particle includes at least two segments, each of which contains a magnetizable material;
applying the magnetic force to at least one segment in order to cause translational motion of the particle; and
applying the magnetic torque to at least one other segment in order to cause rotational motion of the particle,
wherein magnetic torque causing rotation of the at least one particle is decoupled from the magnetic force causing translational motion of the at least one particle, and
wherein a ratio of the resultant translational and rotational velocities of the particle is variable.

12. The method of claim 11, wherein the particle is introduced in a body, and a ratio of the translational and rotational velocities of the particle is varied while the particle is in the body.

13. The method of claim 11, wherein the generation of the magnetic force generates a rotational field ranging from 1 Hz to 1000 Hz.

14. The method of claim 11, wherein the at least one particle is composed of polymeric, metallic, insulating, semiconducting, ceramic, or combinations of at least two of these materials.

15. The method of claim 11, wherein the at least one particle houses electronics, molecules/drugs, proteins, cells, or energy scavenging components.

16. The method of claim 11, wherein at least one of the rotation of the at least one particle and the decoupled translational motion of the at least one particle are implemented in conjunction with the production and application of magnetic fields to apply repulsive and/or propulsive forces so as to manipulate the at least one particle.

17. The method of claim 11, wherein manipulation of the at least one particle is performed by setting up appropriate magnetic gradient fields with or without pre-polarizing pulses.

18. The method of claim 11, wherein the at least one particle is one of a plurality of particles, wherein each particle of the plurality of particles includes some portion or component that contains a magnetizable material, wherein magnetic torque causing rotation of each of the plurality of particle is decoupled from the magnetic force causing translational motion.

19. The method of claim 11, wherein a solution that contains a plurality of particles including the at least one particle, wherein each particle of the plurality of particles includes some portion or component that contains a magnetizable material, wherein magnetic torque causing rotation of each of the plurality of particle is decoupled from the magnetic force causing translational motion.

20. The method of claim 11, wherein an amplitude and frequency of a magnetic field causing rotation of the at least one particle is independent of an amplitude and frequency of a magnetic gradient that is causing translation of the at least one particle.

21. A particle comprising:
at least two magnetic segments,
wherein at least one of the at least two magnetic segments has a length at least twice the diameter of the particle and is magnetized parallel to a major axis of the particle,
wherein at least one other segment of the at least two magnetic segments has a length that is less than the diameter of the particle and is magnetized perpendicular to the major axis of the particle,
wherein magnetization and dimensions of the at least two magnetic segments of the particle configure the particle to be independently rotated and translated in response to application of external magnetic gradients to the particle such that magnetic torque causing rotation of the particle is decoupled from the magnetic force causing translational motion of the particle, and
wherein the ratio of the translational and rotational velocities of the particle is variable.

22. The particle of claim 21, wherein the at least one other segment of the particle is configured to lose magnetization after removal of the magnetic field.

23. The particle of claim 21, wherein the particle is a cylinder and further comprises a non-magnetic material positioned between and separating the at least two magnetic segments along the cylinder major axis.

* * * * *